(12) United States Patent
Jiang et al.

(10) Patent No.: US 9,372,282 B1
(45) Date of Patent: Jun. 21, 2016

(54) STYRENIC OPHTHALMIC AND OTORHINOLARYNGOLOGICAL MATERIALS AND DEVICES FORMED THEREWITH

(75) Inventors: Xuwei Jiang, Arlington, TX (US); Walter R. Laredo, Fort Worth, TX (US)

(73) Assignee: Novartis AG, Basel (CH)

( * ) Notice: Subject to any disclaimer, the term of this patent is extended or adjusted under 35 U.S.C. 154(b) by 220 days.

(21) Appl. No.: 13/596,775

(22) Filed: Aug. 28, 2012

Related U.S. Application Data

(60) Provisional application No. 61/529,412, filed on Aug. 31, 2011.

(51) Int. Cl.
*G02B 1/04* (2006.01)
*G02C 7/04* (2006.01)
*A61F 2/14* (2006.01)
*A61F 2/16* (2006.01)
*A61F 2/18* (2006.01)

(52) U.S. Cl.
CPC . *G02B 1/043* (2013.01); *A61F 2/14* (2013.01); *A61F 2/142* (2013.01); *A61F 2/145* (2013.01); *A61F 2/16* (2013.01); *A61F 2/18* (2013.01); *A61F 2/186* (2013.01); *G02B 1/04* (2013.01); *G02B 1/041* (2013.01); *G02C 7/04* (2013.01); *A61F 2002/183* (2013.01)

(58) Field of Classification Search
CPC .......... G02B 1/04; G02B 1/042; G02B 1/043; G02C 7/04; A61F 2/14; A61F 2/142; A61F 2/145; A61F 2/16; A61F 2/18; A61F 2/186; A61F 2002/183; C08F 212/04; C08F 212/06; C08F 212/08; C08F 212/12; C08F 212/14
USPC .............. 623/6.11, 5.12, 5.11, 5.16, 6.56, 10; 351/159.02; 526/347.1, 347, 346
See application file for complete search history.

(56) References Cited

U.S. PATENT DOCUMENTS

| | | | | |
|---|---|---|---|---|
| 4,611,039 A | * | 9/1986 | Powell | G02B 1/043 264/1.7 |
| 4,616,045 A | * | 10/1986 | Upchurch | C08F 283/12 351/159.33 |
| 5,073,610 A | * | 12/1991 | DuBois | 526/194 |
| 5,331,073 A | | 7/1994 | Weinschenk, III et al. | |
| 5,359,021 A | | 10/1994 | Weinschenk, III et al. | |
| 5,470,932 A | | 11/1995 | Jinkerson | |
| 6,281,319 B1 | * | 8/2001 | Mentak | 526/319 |
| 6,635,731 B2 | | 10/2003 | Mentak | |
| 6,657,029 B2 | | 12/2003 | Vanderbilt | |
| 6,657,032 B2 | | 12/2003 | Vanderbilt | |
| 6,673,886 B2 | | 1/2004 | Vanderbilt | |
| 6,747,090 B2 | | 6/2004 | De Groot et al. | |
| 6,918,931 B2 | | 7/2005 | Lai et al. | |
| 7,033,391 B2 | | 4/2006 | Lai et al. | |
| 2001/0056165 A1 | | 12/2001 | Mentak | |
| 2002/0007032 A1 | | 1/2002 | Mentak | |
| 2002/0037984 A1 | | 3/2002 | Vanderbilt | |
| 2002/0042483 A1 | | 4/2002 | Vanderbilt | |
| 2002/0042484 A1 | | 4/2002 | Vanderbilt | |
| 2002/0049290 A1 | | 4/2002 | Vanderbilt | |
| 2002/0128417 A1 | | 9/2002 | Mentak | |
| 2003/0078657 A1 | | 4/2003 | Zadno-Azizi et al. | |
| 2003/0100666 A1 | | 5/2003 | DeGroot et al. | |
| 2004/0023151 A1 | * | 2/2004 | Takeda et al. | 430/270.1 |
| 2005/0054802 A1 | | 3/2005 | Lai et al. | |
| 2005/0054803 A1 | | 3/2005 | Lai et al. | |
| 2007/0010883 A1 | | 1/2007 | Mentak | |
| 2009/0270876 A1 | * | 10/2009 | Hoffmann et al. | 606/107 |
| 2009/0312836 A1 | * | 12/2009 | Pinchuk et al. | 623/6.37 |

FOREIGN PATENT DOCUMENTS

| | | |
|---|---|---|
| EP | 0667966 | 2/2002 |
| EP | 1177227 | 10/2003 |
| WO | 90/07545 | 7/1990 |
| WO | 90/07575 | 7/1990 |
| WO | 94/11764 | 5/1994 |
| WO | 00/34804 | 6/2000 |
| WO | 00/61646 | 10/2000 |
| WO | 01/05578 | 1/2001 |
| WO | 03/009014 | 1/2003 |
| WO | 2004/010905 | 2/2004 |
| WO | 2005/026182 | 3/2005 |
| WO | 2005/026788 | 3/2005 |
| WO | 2006/025858 | 3/2006 |
| WO | 2006/026325 | 3/2006 |
| WO | 2008/013950 | 1/2008 |

OTHER PUBLICATIONS

Asami et al., "Synthesis of Functional Monomers by Vinylbenzylation and Polymerization of These Monomers", Jpn.—USSR Polym. Symp. [Proc.], 2nd (1976), pp. 249-259.

* cited by examiner

*Primary Examiner* — Roberto Rabago
(74) *Attorney, Agent, or Firm* — Patrick M. Ryan

(57) ABSTRACT

Disclosed are improved ophthalmic and otorhinolaryngological device materials and devices formed therewith. The device materials are soft, high refractive index styrenic device materials that are used to form the ophthalmic or otorhinolaryngological devices, particularly ophthalmic implants (e.g., intraocular lenses).

6 Claims, No Drawings

STYRENIC OPHTHALMIC AND OTORHINOLARYNGOLOGICAL MATERIALS AND DEVICES FORMED THEREWITH

CROSS-REFERENCE TO RELATED APPLICATION

The present application claims priority based on U.S. Provisional Patent Application Ser. No. 61/529,412 filed Aug. 31, 2011.

FIELD OF THE INVENTION

The present invention is directed to improved ophthalmic and otorhinolaryngological device materials and devices formed therewith. In particular, this invention relates to soft, high refractive index styrenic device materials as well as the ophthalmic or otorhinolaryngological devices, particularly ophthalmic implants (e.g., intraocular lenses), formed therewith.

BACKGROUND OF THE INVENTION

With the recent advances in small-incision cataract surgery, increased emphasis has been placed on developing soft, foldable materials suitable for use as intraocular lenses or other ophthalmic implants. Typically, these materials fall into one of three categories: hydrogels, silicones, and acrylics. The intraocular lens (IOL) industry has generally avoided many other materials due to the physical or chemical properties that make those materials unsuitable for use as IOLs. As an example, many materials do not exhibit the desired softness and/or ability to fold that is required when an IOL is folded, stretched and/or compressed for insertion into an eye through a cartridge tip that fits into a small incision in the eye.

Polystyrene is one material that has generally been avoided when forming IOLs. Polystyrene typically has a relatively high glass transition temperature ($T_g$). As such, polystyrene tends to be a hard plastic at human body temperature with little flexibility. This lack of flexibility causes polystyrene to be generally undesirable as an IOL material since it typically cannot be pushed through a small cartridge tip.

Although polystyrene lacks flexibility, it exhibits properties such as high strength, desirable refractive index and lack of biodegradability that are particularly desirable for IOLs. As such, it would be desirable to have a polystyrene material that provided enough flexibility that it could be injected into the eye as an IOL.

One common method of providing flexibility to polystyrene involves the incorporation of one or more flexible materials such as butadiene rubber with the polystyrene. Materials such as butadiene rubber are normally incompatible with polystyrene and cannot be mixed, however, addition of butadiene during the polymerization of polystyrene allows the butadiene to be chemically bonded with the polystyrene. The butadiene can be grafted to the polystyrene backbone or can be integrated into the backbone itself. Such structures are shown below:

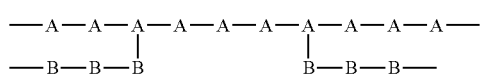

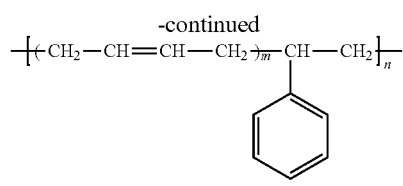

Styrene-butadiene

The resultant styrene-butadiene (SBR) copolymers have excellent mechanical and thermal properties for use as IOLs. Such properties can allow the material to be folded and compressed for insertion through small inner diameters of injection cartridges.

These SBR polymer, however, do suffer from significant drawbacks that make them unsuitable for use as an IOL. SBR polymers include unsaturated carbon-carbon double bonds, which can make them prone to oxidation side reactions. Further, SBR polymers are prone to forming glistenings which can obstruct vision. Further yet, butadiene is a gas under ambient conditions and is therefore very difficult to process into an IOL.

In view of the above, it would be particularly desirable to create a polystyrene material that is suitable for use as an ophthalmic or otorhinolarygological device material and particularly suitable an IOL material.

SUMMARY OF THE INVENTION

Accordingly, there is disclosed a polymeric ophthalmic or otorhinolaryngological device material comprising:

at least 50 w/w % of a polystyrene of structure (I):

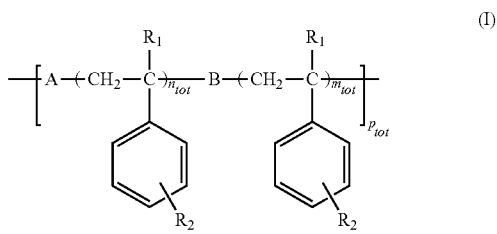

wherein:

$R_1$ independently=H, $CH_3$, or $CH_2CH_3$;

$R_2$ independently=H or $R_3$; and $R_3$ is independently=linear alkyl, branched alkyl, alkyl ether, alkoxy, ester, hydroxy or any combination thereof for each separate combination of values of n and p and m and p where m, n, and p are the separate values of $m_{tot}$, $n_{tot}$, and $p_{tot}$;

A=independently, nothing or a connector moiety;

B=independently, nothing or a connector moiety;

$n_{tot}$=is independently 1 or greater for each value of p;

$m_{tot}$=is independently 1 or greater for each value of p; and $p_{tot}$=2 or greater.

In preferred embodiments, the device material may include any one or a combination of the following characteristics: 1) the polystyrene is cross-linked to form a thermoset polymeric matrix; 2) numerically, $R_2$=$R_3$ at least 75% of the time; 3) the polystyrene of structure (I) can be at least 85% of the device material but no greater than 99% of the device material; 4) numerically, $R_2$=$R_3$ at least 50% of the time; 5) at least, numerically, 50% of $R_3$=alkyl ether, alkoxy or both; 6) the polystyrene of structure (I) is at least 50% but no greater than 97% of the monomers of the device material; and/or $p_{tot}$=50 or greater, 200 or greater or 1000 or greater.

In one embodiment, the device material can include any of the characteristics from above and can be characterized by any one or any combination of the following:
$R_1$=H;
$R_2$=$R_3$ all of the time;
$R_3$ is independently=alkoxy, ester, hydroxy or any combination thereof for each separate combination of values of n and p and m and p;
$R_3$ is independently=alkoxy, ester or a combination thereof for each separate combination of values of n and p and m and p where m, n, and p are the separate values of $m_{tot}$, $n_{tot}$, and $p_{tot}$;
At least a portion of $R_3$=alkyl ether, alkoxy or both
All $R_3$=alkyl ether, alkoxy or both
A=nothing
B=nothing
$M_{tot}$=$n_{tot}$, and/or
$P_{tot}$=5 or greater or 10 or greater or 20 or greater;
In one preferred embodiment, the device material can include any of the characteristics from above and is characterized by each the following:
$R_1$=H;
at least a portion of $R_3$=alkyl ether, alkoxy or both;
A=nothing;
B=nothing; and
$P_{tot}$=5 or greater;
In one preferred embodiment, the device material can include any of the characteristics discussed above and the polystyrene of structure (I) is formed by the polymerization of styrene monomers of the following structure (II):

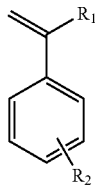
(II)

wherein $R_1$, $R_2$ and $R_3$ are according to any of their descriptions above. In such embodiment, the polystyrene may be formed of at least 40% but no greater than 97% of the monomers of structure (II) polymerized to form the devices materials.

There is also disclosed an ophthalmic or otorhinolaryngological device comprising the device material according to any of the descriptions above wherein the ophthalmic or otorhinolaryngological device is selected from the group consisting of intraocular lenses; contact lenses; keratoprostheses; corneal inlays or rings; otological ventilation tubes; and nasal implants.

Further, there is disclosed a method of forming an ophthalmic or otorhinolaryngological device from a device material, comprising:
combining styrene monomers of the structure (II) as described herein with a polymerization initiator and a cross-linker;
polymerizing the monomers of structure (II) as described herein to form polystyrene of structure (I) as described herein;
cross-linking the polystyrene to form the device material as polystyrene matrix; and forming the device material into the ophthalmic or otorhinolaryngological device either during or after polymerization and/or cross-linking.

The method can be used to form a device wherein the ophthalmic or otorhinolaryngological device is selected from the group consisting of intraocular lenses; contact lenses; keratoprostheses; corneal inlays or rings; otological ventilation tubes; and nasal implants.

DETAILED DESCRIPTION OF THE INVENTION

Unless otherwise specifically stated, polystyrene is intended to encompass any polymeric material that is formed from multiple styrene monomers and includes multiple styrenic units in its polymeric backbone. This will include polystyrene, polystyrene derivatives, and any polymeric material defined by structure (I) above and below.

Unless indicated otherwise, all component amounts are presented on a % (w/w) basis ("wt. %").

The device material of the present invention includes a polystyrene of structure (I) below:
Structure (I)

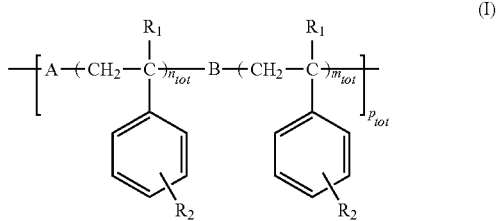

wherein:
$R_1$ independently=H, $CH_3$, or $CH_2CH_3$;
$R_2$ independently=H or $R_3$; and
$R_3$ is independently=linear alkyl, branched alkyl, alkyl ether, alkoxy, ester, hydroxy or any combination thereof for each separate combination of values of n and p and m and p;
A=independently, nothing or a connector moiety;
s B=independently, nothing or a connector moiety;
$n_{tot}$=is independently 1 or greater for each value of p;
$m_{tot}$=is independently 1 or greater for each value of p; and
$p_{tot}$=2 or greater.

Connector moieties suitable for use as A and/or B include, without limitation, acrylics, UV absorber, cross-linkers, other moieties discussed herein, combinations thereof or the like.

To achieve a desired flexibility for the material, it should be the case that $R_2$=$R_3$ rather than hydrogen (H) a substantial portion of the time (i.e., as a numerical amount rather than a w/w %). Numerically, $R_2$=$R_3$ at least 30% of the time, more typically at least 50% of the time, still more typically at least 65% of the time and even possibly at least 75% or even at least 80% of the time. This numerical amount will be equal to the molar or numerical amount of monomers where $R_2$=$R_3$ within the material divided by the sum of the molar or numerical amount of monomers where $R_2$=$R_3$ and the molar or numerical amount of the monomers where $R_2$=H within the material. This is expressed as the ratio below.

$$\frac{\text{Monomers with } R_2 = R_3}{(\text{Monomers with } R_2 = R_3) + (\text{Monomers where } R_2 = H)}$$

which can be multiplied by 100 to yield the numerical percentage.

To achieve desired properties for the device material, it may be desirable to limit the structure (I) with any one or any combination of the following:

$R_1$=H;

$R_2$=$R_3$ all of the time;

$R_3$ is independently=alkoxy, ester, hydroxy or any combination thereof for each separate combination of values of n and p and m and p;

$R_3$ is independently=alkoxy, ester or a combination thereof for each separate combination of values of n and p and m and p;

At least a portion of $R_3$=alkyl ether, alkoxy or both

All $R_3$=alkyl ether, alkoxy or both

A=nothing

B=nothing $M_{tot}$=$n_{tot}$; and/or $P_{tot}$=5 or greater or 10 or greater or 20 or greater;

4) the polystyrene of structure (I) is at least 85% of the device material but typically no greater than 99% of the device material.

For clarity, the phrase "$R_3$ is independently=linear alkyl, branched alkyl, alkyl ether, alkoxy, ester, hydroxy or any combination thereof for each separate combination of values of n and p and m and p" means that $R_3$ can be independently chosen from alkyl, alkoxy, ester or hydroxyl for all the different combinations of n=1 through n=$n_{tot}$ each combined separately with p=1 through p=$p_{tot}$ and all of the different combinations of m=1 through m=$m_{tot}$ each combined separately with p=1 through p=$p_{tot}$. Thus if $p_{tot}$=2, $n_{tot}$=1 and $m_{tot}$=2, $R_3$ can be independently selected for each of the following: (p=1,n=1); (p=2,n=1); (p=1,m=1); (p=1,m=2); (p=2,m=1); (p=2,m=1) as being linear alkyl, branched alkyl, alkyl ether, alkoxy, ester, hydroxyl or a combination thereof. This independent selection system also holds true when $R_3$ is being selected from a smaller subset (e.g., a subset of alkoxy, ester and hydroxy).

One particularly favored subset of structure 1 includes a combination of the following:

$R_1$=H;

at least a portion of $R_3$=alkoxy, alkyl ether or both or at least, numerically, 50% of $R_3$=alkoxy, alkyl ether or both;

A=nothing;

B=nothing; and $P_{tot}$=5 or greater.

wherein the other chemical variations can be chosen from any of the above definitions.

The polystyrene of structure (I) is typically at least 30%, more typically at least 50%, even more typically at least 70% and even possibly at least 85% or even at least 90% of the device material. The polystyrene of structure (I) is typically no greater than 99%, more typically no greater than 97%, even more typically no greater than 95% and even possibly no greater than 85% or even no greater than 60% of the devices material.

The polystyrene of structure (I) is formed by the polymerization of styrene monomers of the following structure (II):

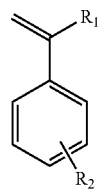

wherein $R_1$, $R_2$ and $R_3$ are according to any of the descriptions above. Thus, the polystyrene of structure (I) is formed in large part from monomers of structure (II).

The polystyrene of structure (I) is typically formed of at least 20%, more typically at least 40%, even more typically at least 60% and even possibly at least 80% or even at least 90% of the monomers of structure (II) polymerized to form the devices materials. The polystyrene of structure (I) is typically formed of no greater than 99%, more typically no greater than 97%, even more typically no greater than 95% and even possibly no greater than 85% or even no greater than 60% of the monomers of structure (II) polymerized to form the devices materials.

Formation of the device materials and/or devices typically includes mixing the monomers of structure (II) with additional ingredients and polymerizing the monomers and preferably curing (i.e., cross-linking) the polymerized monomers (i.e., the polystyrene). It will be understood that polymerization and curing can be carried out concurrently, consecutively or a combination thereof unless otherwise specified. Thus, it shall be understood that the monomers of structure (II), in forming the materials of the present invention, can be formed into oligomers or macromers, copolymers or the like before formation into the final device materials. As suggested, the device materials are preferably cross-linked and, therefore, typically form a cross-linked and/or thermoset matrix, however, it may also be possible to form a device material as a thermoplastic if desired.

Examples of particularly desirable monomers of structure (II) are shown below.

| Styrene Derivative | Polymer Tg (° C.) |
|---|---|
| 1-((2-butoxethoxy)methyl)-4-vinylbenzene | <−38 |
| 1-(butoxymethyl)-4-vinylbenzene | <10 |

| Styrene Derivative | Polymer Tg (° C.) |
|---|---|
| 1-butyl-4-vinylbenzene | 6 |
| 1-decyl-4-vinylbenzene | −65 |
| 1-(ethoxymethyl)-4-vinylbenzene | 0 |
| 1-((octan-3-yloxy)methyl)-4-vinylbenzene | −23 |
| 1-hexadecyl-4-vinylbenzene | 5 |
| 1-(hexyloxymethyl)-4-vinylbenzene | −20 |
| 1-hexyl-4-vinylbenzene | −27 |
| 4-(4-vinylbenzyloxy)butan-1-ol | 20 |
| 1-nonyl-4-vinylbenzene | −53 |
| 1-(octyloxymethyl)-4-vinylbenzene | −42 |
| 1-(octyloxy)-2-vinylbenzene | 13 |
| 1-octyl-4-vinylbenzene | −45 |
| 1-((2-methoxyethoxy)methyl)-4-vinylbenzene | <20 |
| 1-((2-(2-methoxyethoxy)ethoxy)methyl)-4-vinylbenzene | <−30 |
| 1-(hexyloxymethyl)-4-vinylbenzene | −20 |

The device material can comprise, consist essentially of or consist of one or any combination of these exemplary monomers. As the skilled artisan will understand, the monomers, once reacted, will form bracketed styrene groups of structure (I) where R3 is as described.

The styrene monomers of structure (II) can be reacted with various reactive components (e.g., connector moieties such as A and/or B in structure (I)) such as vinyl monomers, co-monomers, macromers, crosslinking agents and the like to form the device materials. Preferred reactive components comprise, without limitation, or consist of compounds that include one or more of the following reactive moieties: a thiol, an acrylate, a methacrylate, a styrenyl, a butadiene, an acrylamide and/or a methacrylamide.

It is contemplated that the device material can additionally include a hydrophilic material to improve glistening resistance. The relatively hydrophilic $R_3$ groups attached to the styrene monomers of the polystyrene can provide glistening resistance, however, in some cases, it may be desirable to include an additional hydrophilic material to further improve glistening resistance. Exemplary hydrophilic components, which may be included in the device material include, without limitation, poly(ethylene glycol) (meth)acrylate, poly(ethylene glycol) monomethyl ether (meth)acrylate, reactive macromers or polymers derived from poly(ethylene glycol), combinations thereof or the like. Such material, when included, will typically comprise at least about 0.1% but no greater than 10% of the device material.

Preferably the device material will include or be formed of cross-linker for cross-linking the polystyrene. The cross-linker can be one or more relatively low molecular weight (i.e., 100 to 500 daltons) compound[s], one or more relatively high molecular weight (i.e., 500 to 6000 daltons) or a combination thereof. Relatively low molecular weight cross-linker includes, without limitation, divinylbenzene, ethylene glycol, dimethacrylate, 1,4-butanediol diacrylate, combinations thereof or the like. When included, relatively low molecular weight cross-linker is typically at least 0.1%, more typically at least 0.5% and even more typically at least 0.8% of the device material, but is typically no greater than 5.0%, more typically no greater than 3.0% and even more typically no greater than 2.2% of the device material. Relatively high molecular weight cross-linker includes, without limitation, poly(ethylene glycol) diacrylate, poly(ethylene glycol) dimethacrylate, combinations thereof or the like. When included, relatively low molecular weight cross-linker is typically at least 1.0%, more typically at least 2.0% and even more typically at least 3.5% of the device material, but is typically no greater than 15%, more typically no greater than 10% and even more typically no greater than 7% of the device material.

The device material of the present invention optionally contains reactive UV absorbers (e.g. benzotriazoles) or reactive colorants. A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1-5% (weight). Suitable reactive blue-light absorbing compounds include those described in U.S. Pat. No. 5,470,932. Blue-light absorbers are typically present in an amount from about 0.01-0.5% (weight). When used to make IOLs, the device materials of the present invention preferably contain both a reactive UV absorber (e.g., a polymerizable UV absorber) and a reactive colorant (e.g., a polymerizable colorant).

In order to form the device material of the present invention, the chosen ingredients are combined and polymerized and/or cross-linked using a radical initiator to initiate polymerization and/or a cross-linker to initiate cross-linking of the polymer by the action of either heat or radiation. The device material is preferably polymerized and/or cross-linked (cured) in de-gassed polypropylene molds under nitrogen or in glass molds.

Suitable polymerization initiators include thermal initiators and photoinitiators. Preferred thermal initiators include peroxy free-radical initiators, such as t-butyl (peroxy-2-ethyl) hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethylbenzoyldiphenyl-phosphine oxide, commercially available as Lucirin® TPO from BASF Corporation (Charlotte, N.C.). Other desirable initiators include azo-type initiators, particularly those with nitrile groups, such as 2,2'-azobisisobutyronitrile or 2,2'-Azobis(2-methylpropionitrile) and 2,2'-Azobis(2.4-dimethyl valeronitrile)Initiators are typically present in an amount equal to about 5% or less of the total formulation weight, and more preferably less than 2% of the total formulation. As is customary for purposes of calculating component amounts, the initiator weight is not included in the formulation weight % calculation.

The particular combination of the ingredients described above and the identity and amount of any additional components are determined by the desired properties of the finished device material. In a preferred embodiment, the device materials of the present invention are used to make IOLs having an optic diameter of at least 4.0 mm, more typically at least 5.0 mm and even possibly at least 6.0 mm but no greater than 9.0 mm, more typically no greater than 7.0 mm and even more typically no greater than 6.6 mm. The IOLS are also preferably capable of being compressed and/or stretched and inserted through surgical incision sizes of 4 mm or less, more typically 3.0 mm or less and even possible 2.2 mm or less.

The device material preferably has a refractive index in the dry state of at least about 1.40, more preferably at least about 1.47, and even more preferably at least about 1.50, as measured by an Abbe' refractometer at 589 nm (Na light source) and 25° C. Optics made from materials having a lower refractive index must often be thicker than desired to achieve desired vision correction and can require relatively larger incisions for IOL implantation.

The device material preferably has an elongation of at least 150%, more preferably at least 300%, and a Young's modulus of less than 6.0 MPa, more preferably less than 5.0 MPa. These properties indicate that a lens made from such material generally will fold easily and will not crack, tear or split when it is folded. Tensile properties of polymer samples are determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using an Instron Material Tester model 4400 with a 50 N load cell. The grip distance is 14 mm and a crosshead speed is 500 mm/minute and the sample is pulled to failure. The elongation (strain) is reported as a fraction of the displacement at failure to the original grip distance ("Elongation" or "Strain at break"). The modulus is calculated as the instantaneous slope of the stress-strain curve at 0% strain ("Young's modulus"), 25% strain ("25% modulus") and 100% strain ("100% modulus"). Tear resistance was measured on unnicked 90° C. angle specimens (Die C) according to ASTM D624-91 "Standard Test Method for Tear Strength of Conventional Vulcanized Rubber and Thermoplastic Elastomers". The test specimens were 20 mm total length, 9.0 mm gauge length and a thickness of 0.9 mm. Testing was performed on samples at standard laboratory conditions of 23±2° C. using an Instron Material Tester model 4400 with a 50 N load cell. The grip distance was 9.0 mm and the crosshead speed was 500 mm/minute and the sample was pulled to failure. The tear resistance ("Tear strength") was calculated from the maximum force obtained during testing divided by the sample thickness.

IOLs constructed of the device materials of the present invention can be of any design capable of being stretched or compressed into a small cross section that can fit through a small incision and/or small cartridge tip (e.g., a cartridge tip having and inner or outer diameter less than 3.2 mm, more typically less than 2.5 mm, even possibly less than 2.2 mm and even possibly less than 2.0 mm). For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

EXAMPLES

IOL Formulations

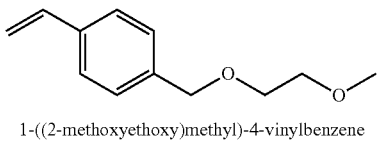

1-((2-methoxyethoxy)methyl)-4-vinylbenzene

Styrene derivative (1) was formulated as shown in Table 1. Test samples measuring 20×10×0.9 mm (length×width×thickness) were made via thermal or photo-curing. Thermally cured samples were cured using a 70° C.→110° C. cure cycle. Samples were first ramp heated from ambient temperature to 70° C. over 15 minutes, soaked at 70° C. for 1 hour, ramp heated from 70° C. to 110° C. over 20 minutes, and then soaked at 110° C. for 2 hours. Photo-cured samples were cured by pre-heating test samples in a nitrogen filled glove box for 10 minutes at 55° C. and then irradiating with a Philips TLK 40W/03 24-inch fluorescent lamp for 60 minutes. Cured samples were extracted in acetone for 20 hours at ambient temperature, dried slowly at ambient temperature for 20 hours, and then vacuum dried at low pressure (0.1 mm Hg) for a minimum of 20 hours at 70° C. Percent extractables were subsequently measured as shown in Table 8. Sample clarity was qualitatively assessed on hydrated lenses using a Dolan-Jenner Fiber-Lite Fiber Optic Illuminator (model 190). Hydrated lenses were placed in the light path while rotating the samples in the x, y, and z directions to determine relative haze.

TABLE 1

| Component | Example (% w/w) | | | | | | |
|---|---|---|---|---|---|---|---|
| | 1A | 1B | 1C | 1D | 1E | 1F | 1G |
| (1) | 96.8 | 96.9 | 96.9 | 96.6 | 82.8 | 67.7 | |
| Divinylbenzene | 1.4 | 1.3 | 1.3 | 1.6 | 1.6 | 1.6 | |
| oMTP | 1.8 | 1.8 | 1.8 | 1.8 | 1.8 | 1.8 | |
| Styrene | 0 | 0 | 0 | 0 | 13.8 | 28.9 | |
| AIBN | 0 | 0 | 0 | 1.0 | 1.0 | 1.0 | |
| Irgacure 819 | 0 | 0 | 0.4 | 0 | 0 | 0 | |
| V-65 | 0 | 1.0 | 0 | 0 | 0 | 0 | |
| Perkadox 16 | 1.0 | 0 | 0 | 0 | 0 | 0 | |

(1) = 1-((2-methoxyethoxy)methyl)-4-vinylbenzene
Irgacure 819 = phenylphosphorylbis(mesitylmethanone)
oMTP = 2-(2H-benzo[d][1,2,3]-triazol-2-yl)-4-methyl-6-(2-methylallyl)phenol
Perkadox 16 = bis(4-tert-butylcyclohexyl) peroxydicarbonate
AIBN = 2,2'-azobisisobutyronitrile or 2,2'-Azobis(2-methylpropionitrile)
V-65 = 2,2'-Azobis(2,4-dimethyl valeronitrile)

TABLE 2

| Example | % Extractables (N ≥ 3) | Refractive Index (35° C.) | Clarity |
|---|---|---|---|
| 1A | 10.1 ± 0.2 | | |
| 1B | 7.8 ± 0.9 | | |
| 1C | 14.2 ± 0.6 | | |
| 1D | 4.1 ± 0.1 | 1.5510 | |
| 1E | 4.8 ± 0.6 | 1.5590 | |
| 1F | 5.0 ± 0.2 | 1.5645 | |
| 1G | | | |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A polymeric ophthalmic or otorhinolaryngological device material comprising:

at least 85 w/w % of a polystyrene of structure (I):

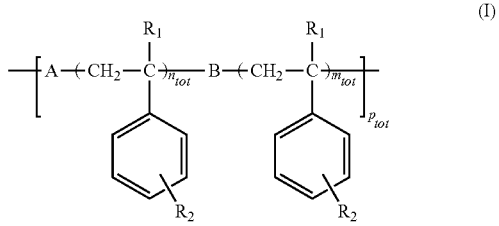

wherein:
$n_{tot}$ represents values of n, which are separate integer values n=1 through n=$n_{tot}$;
$m_{tot}$ represents values of m, which are separate integer values m=1 through m=$m_{tot}$;
$p_{tot}$ represents values of p, which are separate integer values p=1 through p=$p_{tot}$;
$R_1$ independently=H, $CH_3$, or $CH_2CH_3$;

$R_2$ independently=H or $R_3$; and
$R_3$ is independently=linear alkyl, branched alkyl, alkyl ether, alkoxy, ester or any combination thereof for each separate combination of values of n and p and m and p;
A=independently, nothing or a connector moiety;
B=independently, nothing or a connector moiety;
$n_{tot}$=is independently 1 or greater for each value of p;
$m_{tot}$=is independently 1 or greater for each value of p; and
$p_{tot}$=5 or greater; and
wherein, numerically, $R_2=R_3$ at least 50% of the time and wherein the device material is shaped into a device selected from the group consisting of intraocular lenses; contact lenses; keratoprostheses; corneal inlays or rings; otological ventilation tubes; and nasal implants; and
wherein the polystyrene of structure (I) is formed by the polymerization of styrene monomers of the following structure (II):

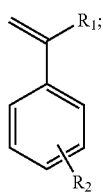

and
wherein the polystyrene of structure (I) is formed from at least 90% but no greater than 97% of the monomers of structure (II) polymerized to form the device material;
wherein the device material has a refractive index in the dry state of at least 1.47, an elongation of at least 150% and a Young's modulus of less than 6.0 MPa.

2. An intraocular lens comprising the device material of claim 1.

3. A method of forming an intraocular lens from a device material, comprising:
providing styrene monomers of structure (II):

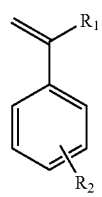

combining styrene monomers of the structure (II) with a polymerization initiator and a cross-linker; and
polymerizing the monomers of structure (II) to form the polystyrene of structure (I):

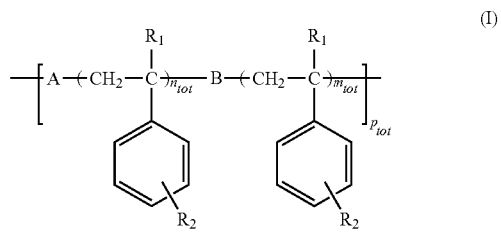

wherein:
$n_{tot}$ represents values of n, which are separate integer values n=1 through n=$n_{tot}$;
$m_{tot}$ represents values of m, which are separate integer values m=1 through m=$m_{tot}$;
$p_{tot}$ represents values of p, which are separate integer values p=1 through p=$p_{tot}$;
$R_1$ independently=H, $CH_3$, or $CH_2CH_3$;
$R_2$ independently=H or $R_3$; and
$R_3$ is independently=linear alkyl, branched alkyl, alkyl ether, alkoxy, ester, hydroxy or any combination thereof for each separate combination of values of n and p and m and p;
A=independently, nothing or a connector moiety;
B=independently, nothing or a connector moiety;
$n_{tot}$=is independently 1 or greater for each value of p;
$m_{tot}$=is independently 1 or greater for each value of p; and
$p_{tot}$=5 or greater; and
wherein, numerically, $R_2=R_3$ at least 50% of the time; and
cross-linking the polystyrene to form the device material as polystyrene matrix wherein at least 85 w/w % of the device material is formed of the polystyrene and wherein the polystyrene is formed from at least 80% monomers of structure (II); and
forming the device material into the intraocular lens either during or after cross-linking.

4. A method as in claim 3 wherein the intraocular lens has an optic diameter of at least 5.0 mm but no greater than 7.0 mm.

5. A method as in claim 3 wherein the intraocular lens is capable of being compressed and/or stretched and inserted through surgical incision sizes of 3.0 mm or less.

6. A lens as in claim 2 wherein the intraocular lens has an optic diameter of at least 4.0 mm but no greater than 9.0 mm.

* * * * *